(12) United States Patent
Schabbach et al.

(10) Patent No.: US 11,419,984 B2
(45) Date of Patent: Aug. 23, 2022

(54) COMPRESSIBLE RESERVOIR FOR LIQUID MEDICAMENT

(71) Applicant: SANOFI-AVENTIS DEUTSCHLAND GMBH, Frankfurt am Main (DE)

(72) Inventors: Michael Schabbach, Frankfurt am Main (DE); Daniel Wagner, Frankfurt am Main (DE); Daniel Auernhammer, Frankfurt am Main (DE); Pierre-Alain Weiss, Schwalbach (DE); Klaus Schepers, Braunfels (DE); Horst Mischo, Trier (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 458 days.

(21) Appl. No.: 15/113,205

(22) PCT Filed: Feb. 11, 2015

(86) PCT No.: PCT/EP2015/052819
§ 371 (c)(1),
(2) Date: Jul. 21, 2016

(87) PCT Pub. No.: WO2015/121275
PCT Pub. Date: Aug. 20, 2015

(65) Prior Publication Data
US 2017/0007767 A1 Jan. 12, 2017

(30) Foreign Application Priority Data
Feb. 12, 2014 (EP) ..................................... 14154777

(51) Int. Cl.
*A61M 5/28* (2006.01)
*A61J 1/14* (2006.01)
(Continued)

(52) U.S. Cl.
CPC .............. *A61M 5/282* (2013.01); *A61J 1/067* (2013.01); *A61J 1/1468* (2015.05); *B29C 45/02* (2013.01);
(Continued)

(58) Field of Classification Search
CPC ........ A61M 5/282; A61J 1/1468; A61J 1/067; A61J 1/1406; B29C 45/02; B29C 45/14;
(Continued)

(56) References Cited

U.S. PATENT DOCUMENTS 2,763,405 A * 9/1956 Shvetz ............... A45D 40/0075
222/320
4,072,249 A * 2/1978 Ekenstam ............. A61M 5/282
222/107
(Continued)

FOREIGN PATENT DOCUMENTS

CN 1863566 11/2006
CN 102066209 5/2011
(Continued)

OTHER PUBLICATIONS

International Search Report and Written Opinion in International Application No. PCT/EP2015/052819, dated Apr. 20, 2015, 12 pages.
(Continued)

*Primary Examiner* — Ariana Zimbouski
(74) *Attorney, Agent, or Firm* — Fish & Richardson P.C.

(57) ABSTRACT

A reservoir for a liquid medicament is described. The reservoir includes a first boundary portion and a second boundary portion forming a cavity to receive the medicament. The first boundary portion is substantially opaque and flexible. The second boundary portion is substantially transparent and rigid.

29 Claims, 3 Drawing Sheets

(51) Int. Cl.
  B65D 1/02      (2006.01)
  B65D 83/00     (2006.01)
  B65D 51/00     (2006.01)
  A61J 1/06      (2006.01)
  B29C 45/02     (2006.01)
  B29C 45/14     (2006.01)
  B29C 70/30     (2006.01)
  B29C 70/52     (2006.01)
  C08J 5/24      (2006.01)
  D06M 15/263    (2006.01)
  B29K 33/00     (2006.01)
  B29K 105/08    (2006.01)

(52) U.S. Cl.
  CPC ............ *B29C 45/14* (2013.01); *B29C 70/305* (2013.01); *B29C 70/52* (2013.01); *B65D 1/0215* (2013.01); *B65D 1/0292* (2013.01); *B65D 51/002* (2013.01); *B65D 83/0094* (2013.01); *C08J 5/24* (2013.01); *D06M 15/263* (2013.01); *A61J 1/1475* (2013.01); *B29K 2033/12* (2013.01); *B29K 2105/08* (2013.01); *C08J 2333/10* (2013.01); *C08J 2333/12* (2013.01)

(58) Field of Classification Search
  CPC .... B29C 70/52; B65D 83/0094; B65D 83/00; B65D 83/0055; C08J 5/24; D06M 15/263; Y10S 215/90; A45D 40/0075
  See application file for complete search history.

(56) References Cited

U.S. PATENT DOCUMENTS

| | | | | |
|---|---|---|---|---|
| 4,153,185 A | * | 5/1979 | Nilson | B65D 83/0094 222/212 |
| 4,230,061 A | * | 10/1980 | Roberts | B63B 11/04 114/74 A |
| 4,282,986 A | * | 8/1981 | af Ekenstam | A61M 5/282 222/1 |
| RE31,785 E | * | 1/1985 | Netteland | A62B 9/022 128/204.26 |
| 4,657,159 A | * | 4/1987 | Grant | B65D 83/00 222/107 |
| 5,470,601 A | * | 11/1995 | Robertson | B65D 51/1616 426/111 |
| 5,482,591 A | * | 1/1996 | Reo | B32B 15/09 156/306.6 |
| 5,964,725 A | * | 10/1999 | Sato | B01D 63/02 422/48 |
| 6,063,058 A | * | 5/2000 | Sakamoto | A61M 5/152 128/DIG. 12 |
| 6,112,752 A | * | 9/2000 | Tahara | A45D 34/00 132/293 |
| 6,544,213 B1 | * | 4/2003 | Lifshey | A61J 1/067 604/89 |
| 6,756,350 B1 | * | 6/2004 | Giblin | B65D 1/0207 428/339 |
| 7,059,487 B2 | * | 6/2006 | Ohlsson | B65D 1/0292 215/381 |
| 2004/0256026 A1 | * | 12/2004 | Py | B29C 66/71 141/329 |
| 2006/0054634 A1 | * | 3/2006 | Mekata | B65D 83/40 222/94 |
| 2006/0155257 A1 | * | 7/2006 | Reynolds | A61J 1/2096 604/414 |
| 2007/0187280 A1 | * | 8/2007 | Haines | A61L 31/10 206/528 |
| 2007/0191780 A1 | * | 8/2007 | Modi | A61M 5/288 604/187 |
| 2008/0167349 A1 | * | 7/2008 | Lippert | A61K 31/44 514/338 |
| 2009/0118682 A1 | | 5/2009 | Hansen et al. | |
| 2010/0004111 A1 | * | 1/2010 | Kobayashi | A01N 59/16 501/32 |
| 2010/0286650 A1 | * | 11/2010 | Fitzgerald | A61J 1/1412 604/500 |
| 2010/0308075 A1 | | 12/2010 | Herold et al. | |
| 2011/0168596 A1 | * | 7/2011 | Fujita | C08K 5/005 206/459.5 |
| 2012/0298675 A1 | * | 11/2012 | Archie, Jr | A47J 36/24 220/592.16 |
| 2013/0075393 A1 | * | 3/2013 | Haynie | B65D 37/00 220/6 |
| 2013/0274576 A1 | | 10/2013 | Amirouche et al. | |
| 2013/0292414 A1 | * | 11/2013 | Sutherland | A47K 5/1201 222/107 |
| 2016/0150868 A1 | * | 6/2016 | Jung | A45D 34/04 222/562 |

FOREIGN PATENT DOCUMENTS

| | | |
|---|---|---|
| EP | 1839695 | 10/2007 |
| EP | 2537545 | 12/2012 |
| GB | 394945 | * 7/1933 |
| GB | 738927 | 10/1955 |
| GB | 1011301 | 11/1965 |
| JP | S51143481 | 12/1976 |
| WO | WO2005/018703 | 3/2005 |
| WO | WO 2005/037185 | 4/2005 |
| WO | WO2006/026684 | 3/2006 |
| WO | WO2009/115467 | 9/2009 |

OTHER PUBLICATIONS

International Preliminary Report on Patentability in International Application No. PCT/EP2015/052819, dated Aug. 16, 2016, 7 pages.

* cited by examiner

COMPRESSIBLE RESERVOIR FOR LIQUID MEDICAMENT

CROSS-REFERENCE TO RELATED APPLICATIONS

This application is a U.S. national stage application under 35 USC § 371 of International Application No. PCT/EP2015/052819, filed on Feb. 11, 2015, which claims priority to European Patent Application No. 14154777.8, filed on Feb. 12, 2014, the entire contents of which are incorporated herein by reference.

DESCRIPTION

Field

The present disclosure relates to the field of reservoirs for liquid medicaments and in particular to reservoirs applicable for long-term storage as well as for administering a liquid medicament by means of a drug delivery device. The disclosure also relates to a respective drug delivery device equipped with such a reservoir

Background and Prior Art

Drug delivery devices for administering liquid medicaments are widely known in the art. Parenteral administering of liquid medicaments is typically conducted by means of injection devices, such like syringes, pen-type injectors or by means of infusion pumps, e.g. by way of micropumps.

For treatment of chronic diseases, such like diabetes the medicament has to be regularly administered according to a predefined schedule. Known drug delivery devices may either be adapted for discrete use for injecting of a predefined amount of the medicament a given number of times during the day. Alternatively, such drug delivery devices may be adapted for continuous or quasi-continuous delivery of the medicament through a permanent fluid connection between the delivery device and the patient. Continuous or constant administering of the medicament is typically conducted by means of infusion pumps that are relatively expensive.

Such drug delivery devices typically comprise a reservoir to accommodate the liquid medicament and having an outlet in fluid communication with some kind of infusion or injection needle. Moreover, such drug delivery devices also comprise a drive mechanism that is operable to expel or to withdraw a predefined amount of the liquid medicament from the reservoir and through the infusion or injection needle into biological tissue of the patient.

There exist reusable as well as disposable devices, wherein with reusable devices the medicament-containing reservoir is to be replaced when empty. With disposable drug delivery devices a pre-filled reservoir is non-detachably arranged in the device. When the medicament contained therein has been used up the entire device is intended to be discarded.

Traditionally, vitreous or glass cartridges have been widely used in injection or infusion systems to contain or to accommodate the liquid medicament, hence a particular pharmaceutical composition. Glass cartridges or carpules provide a large degree of optical transparency and are substantially inert to the medicament. This means, that substantially no interaction between the medicament and the glass cartridge takes place even under long term storage conditions, i.e. when the medicament is stored and contained in the cartridge for time intervals of severely years.

Additionally, the optical transparency of the glass cartridge allows the patient to visually check the quality and integrity of the medicament. Additionally, glass provides an excellent barrier against ingress of liquid or gaseous media from the environment into the cartridge. Moreover, vitreous or glass bodies of cartridges effectively prevent leakage of the medicament from the cartridge. Therefore, vitreous cartridges or glass cartridges are widely used for long-term storage of liquid medicaments. Such cartridges pre-filled with a liquid medicament can be stored over comparatively long time intervals and may be readily assembled with or into a drug delivery device for direct delivery of the medicament from the cartridge into biological tissue of the patient.

Vitreous cartridges or glass cartridges are prone to mechanical impact and may therefore represent a concern for patients but as well for the pharmaceutical industry. Glass breakage typically represents a hazard for the patient as well as for the industrial production environment. Moreover, handling of broken glass is quite risky and dangerous for the persons concerned with a broken cartridge.

Especially with highly concentrated medicaments and with infusion pump applications comparatively small volumes have to be injected or low volume flow rates have to be realized. Extraction and withdrawal of a comparatively small amount of medicament from a vitreous cartridge may be rather elaborate since a piston typically sealing a proximal end of the cartridge is to be displaced in distal, hence in injection direction typically by means of a plunger of the drug delivery device.

Since the piston provides a proximal seal of a cartridge it is only displaceable relative to the barrel of the cartridge against static and/or dynamic friction forces. Especially with miniaturized infusion pumps that may operate in a suction mode for withdrawing the medicament from the reservoir, use of vitreous cartridges sealed with a displaceable piston are rather unsuitable. For such application scenarios use of a deformable or flexible reservoir would be advantageous.

Document US 2009/0118682 A1 describes a reservoir unit comprising a housing and a reservoir arranged at least partially within the housing. There, the reservoir comprises a first transparent area and a second area opposite the first area that comprises a visually non-uniform surface portion. The reservoir comprises first and second flexible foil portions sealed together to form an enclosed cavity for containing the fluid, wherein the reservoir has a pouch-like configuration.

Flexible and transparent foils on the basis of polymers typically do not provide a sufficient barrier against ingress or leakage of gaseous or liquid media into or from such reservoirs. Flexible and transparent pouch-like reservoirs are therefore not applicable or usable as a means for long term storage of liquid medicaments due to their poor barrier properties. Infusion pumps making use of such flexible and transparent reservoirs therefore have to be filled by the patient himself just before use of the medicament.

The insufficient barrier properties of materials that are substantially transparent and flexible impede application of these materials for long term storage of liquid medicaments. However, from a patient's point of view it would be highly desirable and practicable to make use of pre-filled reservoirs ready for use in or with a drug delivery device.

Certain implementations of the subject matter described here can be implemented to provide a reservoir for a liquid medicament which allows for visual inspection of its content, which provides sufficient mechanical strength as well as long term storage stability for the medicament contained therein. Additionally, the reservoir should provide a high barrier, both in terms of moisture and gas. Moreover, the reservoir should be less prone to mechanical impact as compared to vitreous cartridges and should further provide easy extraction of its content even with comparatively low suction forces. Furthermore, the reservoir should not only provide long term storage of the medicament but should also be suitable for drug delivery. It should therefore be compatible with drug delivery devices for medicament delivery to patients.

SUMMARY

In a first aspect a reservoir for a liquid medicament is provided. The reservoir comprises a first boundary portion and a second boundary portion, wherein first and second boundary portions form a cavity to receive the medicament. Here, the first boundary portion is substantially opaque and is also flexible. In contrast to that, the second boundary portion is substantially transparent and rigid. The reservoir therefore comprises a non-uniform structure with first and second boundary portions having different degrees of optical transparency and mechanical strength. By combining first and second boundary portions to form a cavity to accommodate the medicament, the reservoir is at least in sections transparent and is further at least in sections flexible or mechanically deformable in general. Hence, the demands for a reservoir being flexible and transparent simultaneously are effectively fulfilled without making use of a material being flexible and transparent.

Instead, the transparent and flexible properties of the reservoir are separately provided by second and first boundary portions that are selectively transparent or mechanically deformable. By the combination of first and second boundary portions the respective transparent and flexible properties can be unalterably transferred to the reservoir as a whole.

By making use of the first boundary portion being substantially opaque and flexible, said boundary portion can be made of flexible materials or flexible foils that do not need to be transparent. Non-transparent or opaque but mechanically deformable materials to form the first boundary portion may easily provide a sufficient barrier against gaseous and/or liquid media to a required degree which allows for long term storage of the medicament.

In a similar way, by providing the second boundary portion being transparent but rigid, a transparent portion of the reservoir can be provided that does not need to be flexible. As a consequence, transparent but rigid or stiff materials can be used to form the second boundary portion that provides a barrier against gaseous and/or liquid media to a required degree.

The reservoir may be therefore represents a hybrid type reservoir combining the mechanical and optical properties of boundary portions made of different materials.

In the present context, the term boundary portion denotes an arbitrary portion of the reservoir enclosing the medicament receiving cavity thereof. A boundary portion may constitute or may belong to a wall portion of the reservoir. Depending on the geometry of the reservoir the boundary portions may represent sidewall portions, bottom portions or upper portions of the reservoir. Since the reservoir is not limited to a particular geometrical structure, first and second boundary portions may also be of arbitrary shape and geometry as long as they form the medicament receiving cavity. Typically, first and second boundary portions together form a closed or confined volume that coincides with the medicament receiving cavity.

According to an embodiment the first boundary portion is formed by at least one flexible material. Making use of an inherently flexible material is of particular advantage when the reservoir is to be used with an infusion pump arrangement. In this way, the liquid medicament may be easily extracted or withdrawn from the cavity by way of suction. Here, the flexible material of the first boundary portion allows reduction of the size of the cavity of the reservoir as the medicament is extracted continuously or in discrete steps from the reservoir's cavity. The material the first boundary portion is made of may be elastically or plastically deformable. Especially with a plastically deformable flexible material the reservoir would not exhibit any restoring forces that could act against a suction effect of a pump in fluid communication with the reservoir's cavity.

According to another embodiment the first boundary portion is formed by at least one stretchable material. Making use of a stretchable material allows for a variation of the overall size of the first boundary portion. While the medicament is extracted from the cavity the first boundary portion may stretch to reduce the cavity's volume and/or to adapt to the shape and/or geometry of the second boundary portion.

It is generally conceivable, that the reservoir is filled with the medicament to such a degree, that the first boundary portion stretches to a predefined degree. In this way, the stretchable material of the first boundary portion would be applicable to establish or to maintain a particular pressure inside the reservoir's cavity. Moreover, a stretchable first boundary portion can be arbitrarily mechanically deformed, e.g. to fit into a reservoir holder of a corresponding drug delivery device.

Additionally, a stretchable first boundary portion may also be suitable to detect an eventual leakage of the reservoir. If for some reason the reservoir should be subject to leakage, the initially stretched first boundary portion initially inducing an at least slightly raised fluid pressure will inherently serve to expel at least a portion of the liquid medicament. As a consequence, the first boundary portion would become subject to a geometric modification easily discernible by the patient or user of the reservoir.

According to another embodiment the second boundary portion is formed by at least one inflexible, hence by a substantially rigid or stiff material. Making use of an inflexible or rigid material for the second boundary portion allows to make use of such transparent materials that feature a barrier against gaseous and/or liquid media to a required degree.

Furthermore, the substantially rigid or stiff second boundary portion also provides and supports a well-defined handling of the reservoir. Vie the second boundary portion the reservoir may be gripped and/or assembled or coupled in or with a drug delivery device.

Apart from the choice of different materials for the first and second boundary portions, first and second boundary portions may be correspondingly or symmetrically-shaped to form the medicament receiving cavity. However, first and second boundary portions may also be asymmetrically shaped to form the cavity. Depending on the choice of materials for the first and second boundary portion, the thickness of first and second boundary portions may vary. For instance, the first boundary portion may be thinner than the second boundary portion.

Moreover, it is also conceivable, that the thickness of the first boundary portion substantially equals the thickness of the second boundary portion. In other embodiments the first and flexible boundary portion could also exhibit a thickness exceeding the thickness of the second boundary portion. Independent from this, first and/or second boundary portions may comprise a uniform or even non-uniform thickness across their cavity forming surface. Consequently, the first and/or the second boundary portion may comprise sections of different thickness or sections with varying material properties, in particular to accommodate and to correspond with demands of the corresponding drug delivery device.

According to another embodiment the first boundary portion is substantially collapsible onto or into the second boundary portion. Here, at least a section of the first boundary portion is collapsible or foldable onto a section of the second boundary portion. In particular, those sections of first and second boundary portions located adjacent to each other are collapsible onto each other upon extraction and withdrawal of the medicament from the reservoir's cavity.

In a further embodiment the first boundary portion may be almost entirely collapsible onto the second boundary portion. Hence, first and second boundary portions may comprise mutually corresponding surface sections and shapes that allow a crease-free folding or collapsing of the first boundary portion onto or into the second boundary portion. In this way the content of the cavity may be completely, hence residuelessly extracted from the reservoir. Upon collapsing the inside-facing surface of the first boundary portion typically gets in direct contact with the inside-facing surface portion of the second boundary portion. Typically, during constant or repeated extraction of the medicament from the cavity, the first boundary portion folds inwardly.

At least the second boundary portion may further confine or provide a second partition of the reservoir's cavity. The first boundary portion may then stretch across an end of said second partition or may equally form a first partition of the cavity. In this case, first and second volumetric partitions each formed by first and second boundary portions mutually complement to the reservoir's cavity.

In alternative embodiments it is conceivable, that only the second boundary portion forms a second partition of the cavity that is closed by the first boundary portion. For instance, the second boundary portion may comprise a cylindrically or tubular-shaped bottomless barrel, wherein the bottom of said barrel is formed and provided by the first boundary portion. Depending on the overall shape, geometry and flexural behaviour of the first boundary portion, the first boundary portion may either form an outwardly bulged first partition of the cavity in an initial configuration that collapses into the hollow space of the second boundary portion upon extraction of the medicament.

Alternatively, the first boundary portion may extend across the end or interface portion of the second boundary portion facing towards the first boundary portion. In such an embodiment, the first boundary portion may comprise a sheet-like planar structure that may be stretched or sucked into the hollow space of the second boundary portion upon extraction of the medicament.

Collapsing of the first boundary portion is not only beneficial for extraction of the medicament from the reservoir but also for filling the reservoir with the medicament. Initially, even prior to filling of the reservoir, the first boundary portion can be completely collapsed or taken into the second boundary portion, such that the volume confined between oppositely located surface portions of first and second boundary portions is substantially minimized.

In embodiments, wherein the shape and geometry of first and second boundary portions mutually match and wherein the size and geometry of the first boundary portion is substantially equal to the respective size and geometry of the second boundary portion, the volume of the cavity can be almost reduced to zero prior to o filling of the reservoir with the medicament.

Introducing the medicament into the cavity, hence between substantially overlapping sections of first and second boundary portions of the reservoir then leads to a deformation of the first boundary portion thereby increasing the volume of the cavity formed by first and second boundary portions, respectively. Since the initial volume of the cavity may approach zero or some negligible value, a substantially bubble-free filling of the medicament into the cartridge can be easily provided by means of the mechanically deformable and collapsible first boundary portion.

According to another embodiment first and second boundary portions are substantially impervious to gases and fluids. In this way, ingress of moisture and oxygen or other liquids or gases into the reservoir can be effectively prevented. Typically, the barrier provided by first and second boundary portions acts in both directions. Consequently, first and second boundary portions are also operable to prevent leakage of gaseous or liquid media from the cavity of the reservoir. Making use of materials and structures of first and second boundary portions that are substantially impervious to gases and fluids provides a beneficial barrier by way of which the reservoir can be used for long term storage of medicaments, hence for at least one year or even for more than two or three years.

According to another embodiment the reservoir further comprises at least one outlet port in fluid connection with the cavity and intersecting at least one of first and second boundary portions. The at least one outlet port may be provided at an end of the second boundary portion facing away from the first boundary portion. In this way, the outlet port will not be clogged or blocked by the first boundary portion e.g. when collapsing into the second boundary portion during withdrawal of the medicament.

In an alternative embodiment, the outlet port is provided on or in the first boundary portion. Additionally or alternatively the outlet port may also be provided in an interface section of first and second boundary portions. In such an embodiment the outlet port intersects both, first and second boundary portions. The outlet port may be provided with a seal that is either removable or penetrable to provide access to the cavity and to the medicament provided therein. Typically, the outlet port may be sealed with some kind of elastic plug or seal, such like a septum that is penetrable by e.g. an injection needle. When provided as a plug or seal, the outlet port may be arranged in a through opening of the second boundary portion. Then, the plug or seal serves to effectively close the outlet opening of the second boundary portion.

In other embodiments, wherein the outlet port is for instance integrated into the first boundary portion, the outlet port may comprise a tube, e.g. a tube port integrally formed with the mechanically deformable or flexible material of which the first boundary portion is made of. The outlet port may further be equipped and provided with a standardized connector, such like a latch, a screw or a bayonet thread in order to attach the outlet port of the reservoir with some kind of drug delivery mechanism.

According to a further embodiment, the first boundary portion and the second boundary portion are mutually connected or bonded along a circumferentially extending seam.

In embodiments, wherein the second boundary portion comprises a tubular-shaped barrel, the circular end section of the second boundary portion is connected or bonded along its complete outer circumference with the first boundary portion to form the closed cavity. But also in embodiments wherein the second boundary portion comprises a substantially flat-shaped geometry or wherein the second boundary portion comprises cup-, pot- or well-like shape an upper rim of the second boundary portion is typically completely bonded or connected with the first boundary portion to form the closed cavity.

Typically, first and second boundary portions are bonded or welded in a liquid- and/or gas-tight manner. Mutual bonding or welding of first and second boundary portions should not only prevent any leakage of the medicament during storage but also upon drug delivery. The connection of first and second boundary portions should resist any pressure, tension or mechanical stress exerted on the reservoir, especially during extraction, either by suction or by applying pressure to the reservoir for expelling an amount of the medicament. First and second boundary portions can be bonded by at least one of the following methods: heat sealing, hot gas welding, hot plate welding, laser welding, friction welding, vibrational welding, ultrasonic welding, high-frequency welding, solvent welding, or by use of a glue or a tie material.

Moreover, the material's first and second boundary portions are made of should be substantially inert in regard to the medicament to be stored in the reservoir.

Filling of the reservoir typically takes place under aseptic conditions, in particular if the medicament itself is prone to degradation during sterilisation. Filling of the reservoir during manufacture of the reservoir may further help to reduce contamination and particle counts form, e.g. in form fill seal, blow fill seal, co-extrusion blow fill seal or stretch blow fill seal.

In still another embodiment the second boundary portion is dyed. In this way, the second boundary portion may provide a spectral filter for selected wavelength of the electromagnetic spectrum. Having a transparent but dyed second boundary portion the liquid medicament provided in the cavity of the reservoir can be effectively protected against electromagnetic radiation of selected wavelengths that may deteriorate or harm the medicament located in the cavity.

According to a further embodiment, the second boundary portion comprises at least one of a glass or a vitreous material, a rigid and transparent polymeric material or a combination thereof. Hence, the second boundary portion may comprise a vitreous section and a rigid and transparent polymeric section. Typically, at least one or a combination of the following polymeric materials may be used for the second boundary portion: polyethylene (PE), in particular low-density polyethylene (LDPE), linear low-density polyethylene (LLDPE), medium-density polyethylene (MDPE), polypropylene (PP), in particular in form of a homopolymer, random or heterophasic copolymer, cyclic olefin copolymer (COC), cyclic olefin polymers (COP), polymethylene pentane, polyethylene terephthalate (PET), polybutylene terephthalate (PBT), polycarbonates (PC), polystyrene (PS), styrene acrylonitrile resin (SAN), methyl methacrylate-acrylonitrile-butadiene-styrene-polymer (MABS), polyvinyl chloride (PVC).

According to another embodiment, the first boundary portion comprises at least one of an elastomeric material, a flexible thermoplastic material, a layer of polymeric material or combinations, composites and laminates thereof.

In particular, the first boundary portion may comprise at least one of the following materials: thermoplastic elastomers (TPE), silicon rubber, butadiene rubber (BR), styrene butadiene rubber (SBR), styrene-ethylene/butylene-styrene type polymers (SEBS), LDPE, LLDPE, ethylene vinyl acetate (EVA), random copolymers of VP, polybutene-1, COC- or COP-based elastomers.

In particular when the first boundary portion comprises a comparatively thin layer of polymeric material, one of the following materials or combinations thereof can be used to form the first boundary portion: MDPE, high-density polyethylene (HDPE), PP, in form of homopolymer, random or heterophasic copolymers, polybutene-1, COC, COP, polymethylene pentane, PET, Polyethylenterephthalat Glycol (PET-G), PBT, PC, SAN or MABS. In general, the first boundary portion may comprise at least one or a combination of the above mentioned materials.

According to another embodiment, the first boundary portion comprises a multilayer structure. Hence, the first boundary portion comprises at least two substantially overlapping layers of different materials. Here, a combination of comparatively thin layers or foils of even rigid materials, such like MDPE, HDPE, PP, polybutene-1, COC, COP, polymethylene pentane, PET, PET-G, PBT, PC, PS, SAN, MABS and arbitrary combinations thereof can be used to form the first boundary portion. Especially when comprising a multilayer structure, the first boundary portion may also comprise at least one layer of polychlorotrifluoroethylene (PCTFE), polyamide (PA), ethylene-vinyl alcohol (EVOH) or polyparylene that can be used as barrier layer in a multilayer structure.

The barrier properties of said materials can be further improved by the use of passive barrier additives, such as polymer platelets of e.g. PA or EVOH, inorganic fillers, such as $SiO_2$, talc, and/or nanocomposites, such like nanoclays. Moreover, also active barrier additives, such as molecular sieves or chemical reactants, including oxidizable compounds may help to reduce the ingress of gaseous or liquid substances. Alternatively or in addition, coatings or laminates are generally applicable to improve the barrier properties of the first boundary portion.

According to a further embodiment, the first boundary portion may therefore comprise at least one metal foil, typically an opaque metal foil. In effect, the first boundary portion may be laminated with a metal foil or may be even metallized, e.g. with aluminum, metal oxides or metal nitrides, that may be summarized as $MO_wN_xC_yH_z$, wherein M represents a single or a combination of metals. In this way, the first boundary portion may comprise a foil or a layer of $SiO_x$, $SiO_xC_yH_z$, $SiO_xN_y$, $SiN_x$, $AlO_x$, $TiO_x$.

Making use of a metal layer, e.g. in form of a metal foil or a metallic coating, the barrier properties of the first boundary portion may be further improved. Additionally, use of metal foils may provide a cost efficient approach to manufacture such reservoirs.

According to another embodiment, the first boundary portion at least in sections is laminated or coated. Typically, the complete first boundary portion is laminated or coated, either with a metallic coating or with an inorganic coating. Typically, the coating may comprise carbon, metal oxides or metal nitrides, partly with organic components, that can be summarised as $MO_wN_xC_yH_z$, in which M represents a single or a combination of metals. Additionally or alternatively also organic coatings, such like polyparylene, epoxy or epoxy amine resins can be used here. Moreover or alternative, the outer or inner surface of the first boundary portion may be chemically modified. Here, a chemical surface modification, such as fluorination of polymers can be used to improve the barrier properties of the first boundary portion.

Production of the first boundary portion and of the second boundary portion may be conducted separately. The first boundary portion may be manufactured by way of extrusion, extrusion blowing or casting while production of the second boundary portion may include at least one of the following production processes: extrusion, extrusion blow molding, injection blow molding, injection molding, compression molding or thermal forming. Additionally and optionally manufacturing processes comprising an orientation step such as in the production of blown, double bubble or bi-oriented film or in stretch blow molding of hollow articles may be further helpful to improve transparency and barrier properties in addition to the mechanical properties of the second boundary portion.

According to another embodiment, the cavity of the reservoir is at least partially filled with the liquid medicament. In particular, the reservoir is pre-filled with the liquid medicament. Moreover and when designed as a reservoir to be coupled with an infusion pump, the reservoir may comprise a comparatively small cavity volume of less than 10 ml, less than 5 ml or less than 3 ml.

By having first and second boundary portions separately providing visual inspection of the content of the reservoir and supporting and allowing a mechanical deformation thereof during medicament extraction, the reservoir can be manufactured by making use of materials being long-term tested in the pharmaceutical environment. This allows to manufacture pre-filled reservoirs that are applicable for long-term storage as well as for immediate application with drug delivery devices, such like infusion pumps or pen-type injectors.

According to another aspect the disclosure also relates to a drug delivery device for dispensing of a liquid medicament. The drug delivery device is typically adapted to receive and/or to engage with the reservoir to extract or to expel a predefined amount of the medicament therefrom. The drug delivery device is typically designed as an injection or infusion device. It may be operable to apply a pressure to the reservoir for expelling the medicament or it may be operable to withdraw the liquid medicament from the reservoir in a suction mode. The drug delivery device may comprise a pen-type injector or an infusion pump.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu- Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38 Exendin-4(1-39)-NH2,
H-(Lys)6-des Pro36, Pro38 [Asp28] Exendin-4(1-39)-NH2, H-Asn-(Glu)5 des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences"17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present disclosure without departing from the spirit and scope of the disclosure. Further, it is to be noted, that any reference signs used in the appended claims are not to be construed as limiting the scope of the present disclosure.

BRIEF DESCRIPTION OF THE DRAWINGS

In the following, various embodiments of the present disclosure will be explained in greater detail by making reference to the drawings, in which.

DETAILED DESCRIPTION

Figure 1:
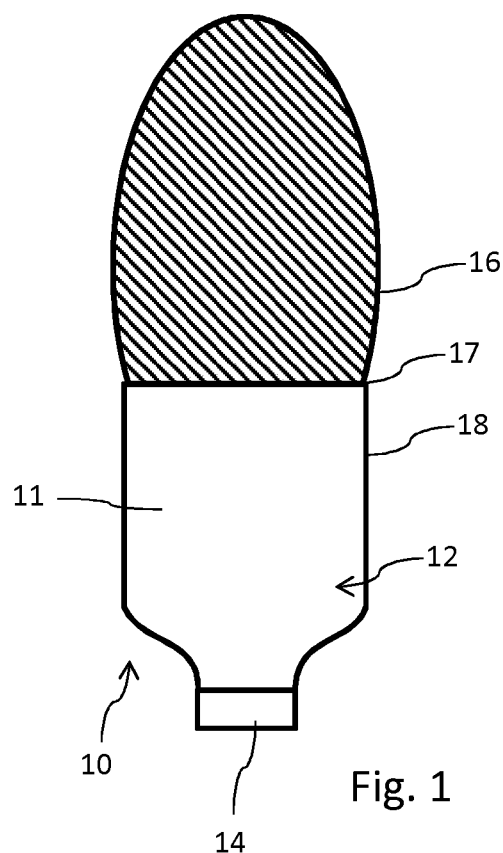
FIG. 1 shows a first embodiment of the reservoir in an initial configuration.

In FIG. 1, a reservoir 10 is schematically illustrated that comprises a first or upper boundary portion 16 and a second or lower boundary portion 18. Both, first and second boundary portions, 16, 18 form a common cavity 12 that is adapted to receive and to accommodate a liquid medicament 11. The first boundary portion 16 features a balloon-like geometrical structure. It seals and closes the upward-facing end of the second boundary portion 18, which in the embodiment according to FIGS. 1-3 comprises a tubular-shaped barrel. While the first boundary portion 16 is substantially opaque and flexible the second boundary portion 18 is substantially transparent and rigid. In this way, the interior of the reservoir 10, hence the medicament 11 contained in the cavity 12 can be visually inspected through the second boundary portion 18 while the first boundary portion 16 imparts a certain flexibility to the reservoir 10.

At its bottom portion facing away from the first boundary portion 16, the second boundary portion 18 comprises an outlet port 14. In the embodiment according to FIGS. 1-3, said outlet port 14 may comprise a pierceable or removable seal, such like a septum or a plug, by way of which access to the cavity 12 can be provided. The reservoir 10, in particular its outlet port 14 may be coupled with some kind of extraction element, such like an injection needle penetrating a sealing disc of the outlet port 14.

Figure 2:
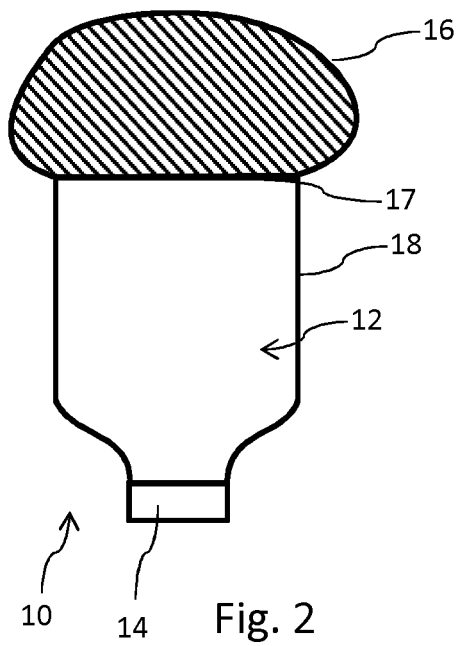
FIG. 2 shows the reservoir according to FIG. 1 during medicament extraction and FIG. 3 shows the reservoir according to FIG. 1 when substantially emptied.

In this way, the medicament 11 may either be extracted or expelled from the cavity, e.g. by applying pressure to the first boundary portion 16 from outside or by applying a suction force through the injection needle towards the interior of the cavity 12. In either way, withdrawal of the medicament from the cavity 12 leads to a mechanical deformation of the first boundary portion 16 as indicated in FIG. 2.

Figure 3:
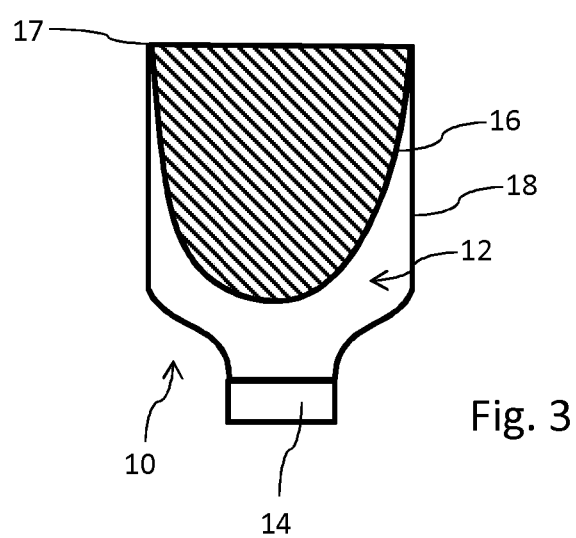

During constant or repeated discrete extraction of the medicament from the cavity 12, the first boundary portion 16 may also collapse into the second boundary portion 18 as illustrated in FIG. 3. Here, the second boundary portion 18 forms a second partition of the cavity 12 and forms a hollow space into which the first boundary portion 16, which initially forms a first partition of the cavity 12, may extend upon medicament extraction. In this way, the volume of the cavity 12 may constantly reduce during extraction of the medicament 11. Since the first boundary portion 16 is flexible or even stretchable it may completely adopt the shape and contour of the inward-facing surface or surface structure of the second boundary portion 18. In this way, the complete content of the reservoir 10 can be expelled and extracted from the reservoir 10.

The collapsing of the first boundary portion 16 into the second boundary portion 18 or onto the inward-facing wall structure of the second boundary portion 18 is also beneficial for filling of the reservoir 10. Especially when the first boundary portion 16 adopts the geometric shape of the second boundary portion 18 in a crease-free way, a substantially bubble-free filling of the reservoir 10 with the medicament 11 can be obtained.

First and second boundary portions 16, 18 are typically bonded or welded in a non-releasable way. Since the second boundary portion 18 is of substantially tubular-shape and since the second boundary portion 18 comprises a substantially circular cross-section, the first boundary portion 16 is connected with the second boundary portion along a circumferentially extending seam 17, which is only shown from the side in FIGS. 1-3.

Figure 4:
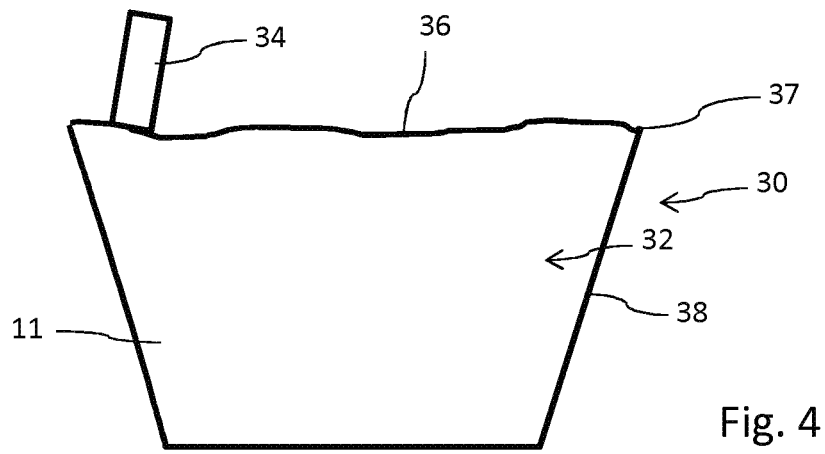
FIG. 4 shows another embodiment of a reservoir in an initial configuration.
Figure 5:
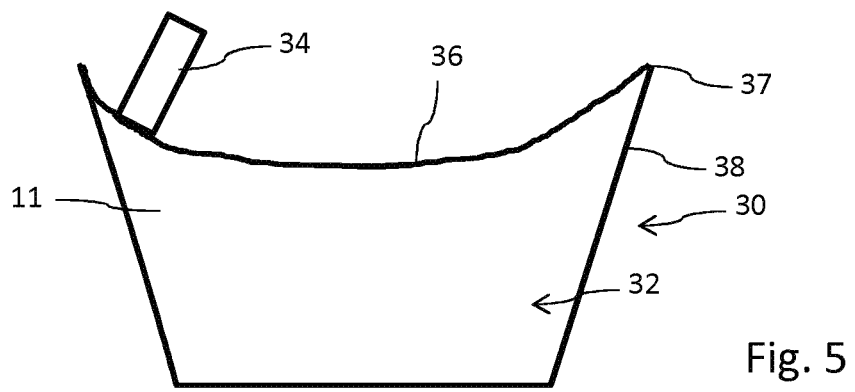
FIG. 5 shows the reservoir according to FIG. 4 during medicament extraction.
Figure 6:
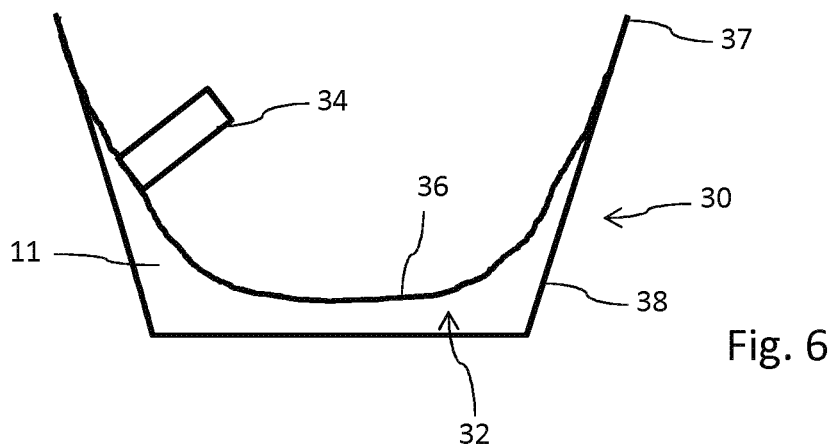
FIG. 6 shows the reservoir according to FIGS. 4 and 5 when substantially empty, FIG. 7 schematically shows another embodiment of a reservoir in an initial configuration

In an alternative embodiment as illustrated in FIGS. 4-6, the reservoir 30 also comprises a cavity 32 that is formed by a first boundary portion 36 and by a second boundary portion 38. But here and in contrast to the embodiment according to FIGS. 1-3 it is the first boundary portion 36 that is provided with the outlet port 34. Here, the outlet port 34 is designed as an outlet tube that may be integrally formed with the flexible first boundary portion 36. However, the outlet port 34 may also be integrated in the second boundary portion 38.

Additionally and further in contrast to the embodiment according to FIGS. 1-3, the first boundary portion 36 is initially substantially planar-shaped or flat-shaped and serves as a kind of lid of the pot-shaped or cup-shaped second boundary portion 38. However, as the medicament is extracted via the outlet port 34 from the cavity 32, the flexible first boundary portion 36 becomes subject to mechanical deformation and may sink or collapse into the second boundary portion 38. Also here, when reaching an end of content configuration, i.e. when the reservoir 30 is almost empty, the first boundary portion 36 may adopt or adapt to the geometric shape of the second boundary portion 38. Here, an outlet port 34 is arranged offset from the center of the reservoir 30 but may be also arranged symmetric in regard of the circumferential seam 37 along which first and second boundary portions 36, 38 are non-releasably interconnected, bonded or welded.

In the embodiment according to FIGS. 4-6, the second boundary portion 38 comprises substantially planar-shaped bottom and sidewall portions extending upwardly and outwardly. Consequently, the lateral extension of the first boundary portion 36 interconnected with the upper end of the sidewall portions of the second boundary portion 38 is substantially larger than the corresponding extent of the second boundary portion's 38 bottom section. The bottom section may be of rectangular or polygon shape or may even be elliptic or circular.

Since the first boundary portion 36 is connected or bonded to the upper end of the second boundary portion's 38 sidewall or sidewalls along a seam 37, the first boundary portion experiences a respective stretching when collapsing into the second boundary portion 38 during extraction of the medicament 11. Here, it is of particular benefit, when the first boundary portion is formed of at least one stretchable material.

Additionally and as already described in connection with the embodiment according to FIGS. 1-3, the first boundary portion 36 is substantially opaque and is further mechanically deformable while the second boundary portion 38 is substantially transparent and rigid or stiff.

Figure 7:
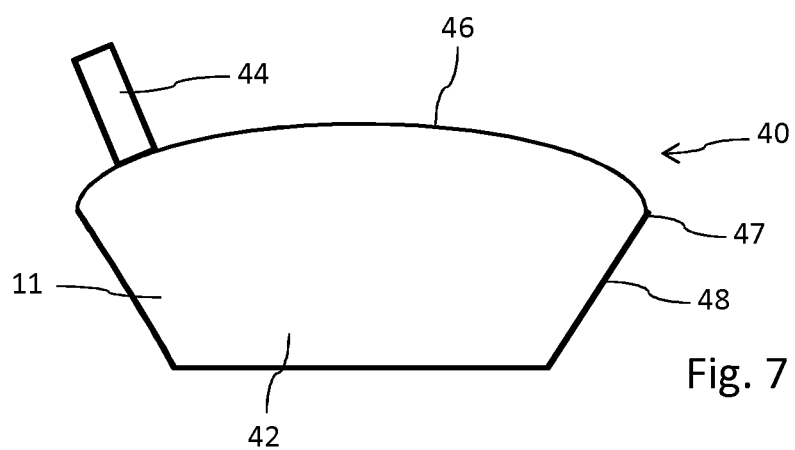
Figure 8:
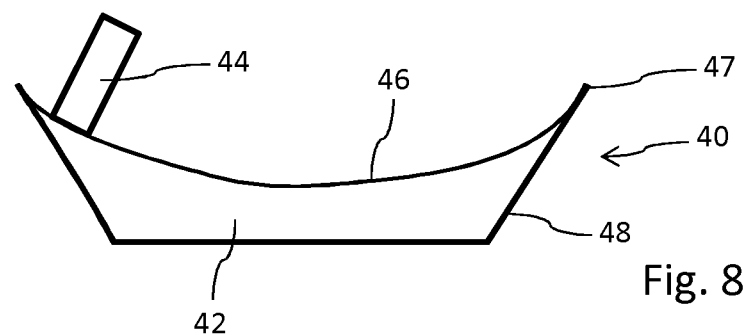
FIG. 8 shows the reservoir according to FIG. 7 when almost empty.

The embodiment according to FIGS. 7 and 8 slightly differs from the embodiment according to FIGS. 4-6 in that the first boundary portion 46 of the reservoir 40 is initially upwardly or outwardly stretched or bulged when filled with the medicament 11. Also here, the second boundary portion 48 comprises a cup- or pot-like shape with a planar bottom section and with an upwardly extending sidewall. Again, the upper end of the second boundary portion's 48 sidewall section is bonded or welded with the first and flexible boundary portion 46 along a seam 47. Since the first boundary portion 46 is initially outwardly or upwardly bulged, it extends away from the second boundary portion 48.

Additionally, the outlet port 44 intersects the first boundary portion 46 for the purpose of extracting the medicament 11 from the cavity 42. As becomes apparent from FIG. 8, extraction of the medicament 11 leads to a reduction of the volume of the cavity 42, thereby inducing a collapsing of the first boundary portion 46 into the receptacle-forming second boundary portion 48.

Since the first boundary portion 46 was initially outwardly bulged its surface is substantially larger than the cross-section of the second boundary portion's 48 upper end. In this way, the first boundary portion 46 may easily collapse into the second boundary portion 48 even without the necessity of stretching or increasing its size. In particular, the first boundary portion 46 may comprise a surface substantially equal in size to the surface of the inward-facing sections of the second boundary portion 48. Then the first boundary portion 46 may completely collapse and engage with the second boundary portion 48 in a crease-free way while reducing the volume of the cavity 42 to a minimum.

LIST OF REFERENCE NUMERALS 10 reservoir
11 medicament
12 cavity
14 outlet port
16 first boundary portion
17 seam
18 second boundary portion
30 reservoir
32 cavity
34 outlet port
36 first boundary portion
37 seam
38 second boundary portion
40 reservoir
42 cavity
44 outlet port
46 first boundary portion
47 seam
48 second boundary portion

The invention claimed is:

1. A reservoir for a liquid medicament, the reservoir comprising:
   a first boundary portion,
   a second boundary portion, wherein the first boundary portion and the second boundary portion form a cavity to receive the medicament, and
   at least one outlet port in fluid connection with the cavity and intersecting the first boundary portion, wherein the at least one outlet port comprises a tube port integrally formed with the first boundary portion,
   wherein the first boundary portion is opaque and flexible, and
   wherein the second boundary portion is transparent and rigid.

2. The reservoir according to claim 1, wherein the first boundary portion is stretchable.

3. The reservoir according to claim 1, wherein the second boundary portion comprises at least one inflexible material.

4. The reservoir according to claim 1, wherein the first boundary portion is collapsible onto or into the second boundary portion.

5. The reservoir according to claim 1, wherein the first boundary portion and the second boundary portion are impervious to gases and fluids.

6. The reservoir according to claim 1, wherein the second boundary portion is dyed.

7. The reservoir according to claim 1, wherein the second boundary portion comprises a glass or a rigid and transparent polymeric material.

8. The reservoir according to claim 1, wherein the first boundary portion comprises at least one of an elastomeric material, a flexible thermoplastic material or a polymeric material.

9. The reservoir according to claim 1, wherein the first boundary portion comprises a multilayer structure.

10. The reservoir according to claim 9, wherein the first boundary portion comprises an opaque metal foil.

11. The reservoir according to claim 9, wherein the first boundary portion is laminated or coated.

12. The reservoir according to claim 1, wherein the cavity is at least partially filled with the liquid medicament.

13. A reservoir for a liquid medicament, the reservoir comprising:
   a first boundary portion,
   a second boundary portion forming a cavity to receive the medicament, and
   at least one outlet port in fluid connection with the cavity and intersecting the first boundary portion, wherein the at least one outlet port comprises a tube port integrally formed with the first boundary portion,
   wherein the first boundary portion is opaque and flexible, and
   wherein the second boundary portion is transparent and rigid.

14. The reservoir according to claim 1, wherein the at least one outlet port is integrated into the first boundary portion.

15. The reservoir according to claim 1, wherein the at least one outlet port is equipped and provided with a connector comprising one of a latch, a screw or a bayonet thread.

16. The reservoir according to claim 1, wherein the at least one outlet port is sealed with an elastic plug or seal penetrable by an injection needle.

17. The reservoir according to claim 1, wherein the tube port protrudes outwardly from the first boundary portion.

18. The reservoir according to claim 1, wherein the first boundary portion and the second boundary portion are mutually bonded along a circumferentially extending seam.

19. The reservoir according to claim 1, wherein the tube port comprises a mechanically deformable or flexible material of which the first boundary portion is made of.

20. The reservoir according to claim 1, wherein the tube port comprises a flexible tube.

21. The reservoir according to claim 1, wherein the first boundary portion is planar-shaped before the medicament is extracted though the at least one outlet port.

22. The reservoir according to claim 13, wherein the first boundary portion and the second boundary portion are mutually bonded along a circumferentially extending seam.

23. The reservoir according to claim 13, wherein the tube port comprises a mechanically deformable or flexible material of which the first boundary portion is made of.

24. A reservoir for a liquid medicament, the reservoir comprising:
   a first boundary portion,
   a second boundary portion, wherein the first boundary portion and the second boundary portion form a cavity to receive the medicament, and
   at least one outlet port in fluid connection with the cavity and intersecting the first boundary portion,
   wherein the first boundary portion is opaque and flexible,
   wherein the second boundary portion is transparent and rigid,
   wherein the first boundary portion and the second boundary portion are mutually bonded along a circumferentially extending seam, and
   wherein the outlet port is equipped and provided with a connector comprising one of a latch, a screw or a bayonet thread.

25. The reservoir according to claim 1, wherein the first boundary portion and the second boundary portion define a closed volume that forms the cavity such that the medicament is configured to contact the first and second boundary portions.

26. The reservoir according to claim 1, wherein the medicament is within the cavity, wherein the medicament includes at least one pharmaceutically active compound.

27. The reservoir according to claim 1, wherein the first boundary portion is initially of a planar or flat shape and forms a lid of the second boundary portion, wherein the second boundary portion is cup-shaped.

28. The reservoir according to claim 1, wherein the first boundary portion is configured to deform from a planar shape to a shape defined by an inside surface of the second boundary portion.

29. The reservoir according to claim 15, wherein the connector is configured to attach the outlet port with one of an injection device or an infusion device.

* * * * *